(12) United States Patent
Kuhl et al.

(10) Patent No.: US 11,123,000 B2
(45) Date of Patent: Sep. 21, 2021

(54) DIGITAL BIOPOTENTIAL ACQUISITION SYSTEM HAVING 8 CHANNELS

(71) Applicant: Neuroloop GmbH, Freiburg (DE)

(72) Inventors: Matthias Kuhl, Freiburg (DE);
Yiannos Manoli, Freiburg (DE);
Dennis Plachta, Vörstetten (DE);
Thomas Stieglitz, Freiburg (DE);
Oscar Cota, Freiburg (DE)

(73) Assignee: NEUROLOOP GMBH, Freiburg (DE)

( * ) Notice: Subject to any disclaimer, the term of this patent is extended or adjusted under 35 U.S.C. 154(b) by 102 days.

(21) Appl. No.: 16/078,541

(22) PCT Filed: Feb. 22, 2017

(86) PCT No.: PCT/EP2017/054057
§ 371 (c)(1),
(2) Date: Aug. 21, 2018

(87) PCT Pub. No.: WO2017/144529
PCT Pub. Date: Aug. 31, 2017

(65) Prior Publication Data
US 2019/0059755 A1 Feb. 28, 2019

(30) Foreign Application Priority Data
Feb. 22, 2016 (DE) ...................... 10 2016 103 073.2

(51) Int. Cl.
*A61B 5/24* (2021.01)
*A61B 5/00* (2006.01)
(Continued)

(52) U.S. Cl.
CPC ................ *A61B 5/24* (2021.01); *A61B 5/333* (2021.01); *A61B 5/389* (2021.01); *A61B 5/7203* (2013.01);
(Continued)

(58) Field of Classification Search
CPC . A61B 5/04001; A61B 5/0432; A61B 5/0488; H03F 3/45179; H03F 2200/129;
(Continued)

(56) References Cited

U.S. PATENT DOCUMENTS

| | | |
|---|---|---|
| 5,479,137 A | 12/1995 | Harford |
| 7,385,443 B1 | 6/2008 | Denison |

(Continued)

FOREIGN PATENT DOCUMENTS

| | | |
|---|---|---|
| EP | 1312303 A2 | 5/2003 |
| JP | H061 97877 A | 7/1994 |

(Continued)

OTHER PUBLICATIONS

Aziz et al., "Multi-Channel Integrated Neural Interfaces for Distributed Electro-Chemical Sensing", Circuits and Systems (ISCAS), International IEEE Symposium, IEEE, 2006—pp. 1782-1785.

(Continued)

*Primary Examiner* — Catherine M Voorhees
*Assistant Examiner* — Roland Dinga

(57) ABSTRACT

A biocompatible recording system includes a number of input channels for acquiring electronic information from the neural system of a living being. The recording system includes a preamplifier and further amplifier stages. An input of a second amplifier stage is coupled to an output of the preamplifier. A low-pass filter having a capacitance multiplier is connected to the second amplifier stage. The preamplifier of the recording system is designed using P-MOS technology.

7 Claims, 17 Drawing Sheets

Block diagram of the LN8 recording system

(51) Int. Cl.
  *A61B 5/333* (2021.01)
  *A61B 5/389* (2021.01)
  *H03F 3/45* (2006.01)
(52) U.S. Cl.
  CPC ........ *H03F 3/45179* (2013.01); *A61B 5/6846* (2013.01); *H03F 2200/129* (2013.01); *H03F 2200/144* (2013.01); *H03F 2200/171* (2013.01); *H03F 2203/45024* (2013.01); *H03F 2203/45116* (2013.01); *H03F 2203/45526* (2013.01)
(58) Field of Classification Search
  CPC ......... H03F 2200/144; H03F 2200/171; H03F 2203/45024; H03F 2203/45116; H03F 2203/45526
  See application file for complete search history.

(56) References Cited

U.S. PATENT DOCUMENTS

| | | | |
|---|---|---|---|
| 8,436,679 | B1 | 5/2013 | Alzaher et al. |
| 2003/0097050 | A1 | 5/2003 | Fassio |
| 2003/0210092 | A1* | 11/2003 | Mehr .................. H03F 3/45188 330/9 |
| 2005/0116773 | A1 | 6/2005 | Laletin |
| 2006/0087345 | A1 | 4/2006 | Schoenbauer |
| 2010/0106041 | A1 | 4/2010 | Ghovanloo et al. |
| 2014/0180052 | A1 | 6/2014 | Lo et al. |
| 2014/0330102 | A1 | 11/2014 | Zbrzeski et al. |
| 2015/0372651 | A1* | 12/2015 | Hsieh .................. H03F 3/45183 341/155 |

FOREIGN PATENT DOCUMENTS

| | | |
|---|---|---|
| JP | H07226626 A | 8/1995 |
| JP | H08215164 A | 8/1996 |
| JP | 2006121714 A | 5/2006 |
| JP | 2014517659 A | 7/2014 |

OTHER PUBLICATIONS

Baharudin et al., "Design and Analysis of a Two-Stage OTA for Senior Interface Circuit", 2014 IEEE Symposium on Computer Applications and Industrial Electronics (ISCAIE), Apr. 30, 2014—pp. 1-5.
Cota et al., "In-Vivo Characterization of a 0.8-3 μ VRMS Input-Noise Versatile CMOS Pre-Amplifier," Neural Engineering (NER), 2015 7th International IEEE/EMBS Conference, 2015—pp. 458-461.
German Search Report for Application No. 10 2016 103 073.2, dated Jan. 30, 2017, with translation—15 pages.
International Search Report and Written Opinion for International Application No. PCT/EP2017/054057, dated May 4, 2017—9 pages.
Maghami et al., "Fully-Integrated, Large-Time-Constant, Low-PAss Gm-C Filter Based on Current Conveyors", Electronics, Circuits and Systems (ICECS), 18th IEEE International Conference, IEEE 2011—pp. 281-284.
Ramirez-Angulo et al., "Gain Programmable Current Mirrors Based on Current Steering," Electronics Letters, 2006, vol. 42, No. 10—pp. 559-560.
Razavi, B., Design of Analog CMOS Integrated Circuits: Tata McGraw-Hill Education, 2002—pp. 1-706.
Zhang et al., "Design of Ultra-Low Power Biopotential Amplifiers for Biosignal Acquisition Applications," IEEE Transactions on Biomedical Circuits and Systems, 2012, vol. 6, No. 4—pp. 344-355.
Taylor et al., "A Low-Noise Front-End for Multiplexed ENG Recording using CMOS Technology," Analog Integrated Circuits and Signal Processing, 2011, vol. 68, No. 2—pp. 163-174.
Harpe, P., et al., "A 3nW Signal-Acquisition IC Integrating an Amplifier with 2.1 NEF and a 1.5fJ/conv-step ADC," Feb. 25, 2015, pp. 382-384, 2015 IEEE Intl. Solid-State Circuits Conference / Session 21 / Innovative Personalized Biomedical Systems / 21.2.
Ruiz, J.A., et al., "Three Novel Improved CMOS Capacitance Scaling Schemes," 2010, 5 pages, Proceedings of 2010 IEEE International Symposium on Circuits and Systems.
Yin, M., et al., "A Low-Noise Clockless Simultaneous 32-Channel Wireless Neural Recording System with Adjustable Resolution," 2011, pp. 417-431, vol. 66, Analog Integrated Circuits and Signal Processing.
Yang, Xiao et al., "An Amplifier Design Suitable for ECG Signal Detection," School of Information Science and Engineering, Journal of Huaqiao University (Natural Science), vol. 32, No. 6, Nov. 2011, 12 pages.
Japanese Office Action received in Application No. 2018-562715 dated Jan. 25, 2021, 10 pages.
Chinese Office Action received in Application No. 201780012702.3 dated Oct. 30, 2020, 11 pages.
Chinese Search Report received in Application No. 2017800127023 dated Oct. 20, 2020, 13 pages.
Cota, et al., "In-vivo characterization of a 0.8-3 VRMS input-noise versatile CMOS pre-amplifier," 2015 7th International IEE/EMBS Conference on Neural Engineering (NER) dated Apr. 22-24, 2015, 5 pages.
Office Action received in Chinese Application No. 201780012702.3 dated Jun. 15, 2021, with translation, 16 pages.

\* cited by examiner

Block diagram of the LN8 recording system

Telescopic with feedback circuit

FD telescopic PMOS Transistor layer

Performance curves for
predefined noise behaviour

Second stage

Second stage OTA

Signal paths from amplifier outputs to serial digital outputs

Microscope image of the chip with 8 bipolar input channels

| Analog | | Digital | | Test (analog) | |
|---|---|---|---|---|---|
| (D, A) $V_{DD}$ | 3 | $I_{SS}$ (T1-T4) | 4 | $V_{EXT\_CMFB}$ | |
| (D, A) $V_{SS}$ | 3 | $V\_REF\_ISS\_EN$ | | $V_{DD\_ISS(1,5)}$ | 2 |
| $V_{REF\_ISS}$ | | LP_EN | | $V_{OUTN/P(1,5)}$ | 2 |
| $V_{IN(N/P)(1-8)}$ | 16 | RESET_EN | | $V_{OUT1/5}$ | 2 |
| $V_{REF\_CMFB}$ | | GAIN_0dB_EN | | Test (digital) | |
| $V_{GCP/N}$ | 2 | CAP_MULT_EN | | RESET ADC | |
| $V_{TUNE}$ | | CLK | | $Q1_{0-3}$ | 4 |
| $V_{REFH}$ | | $CHSEL_{0-3}$ | 4 | EOC1 | |
| $V_{REFL}$ | | DS OUT (1/2) | 2 | SW1 | |

I/O pins of the LNA8 chip

Fig. 9

| System | Gain /dB | Noise /μV$_{RMS}$ | Power / Channel /μW | fcL /Hz | fcU /Hz | CMRR /dB | NEF |
|---|---|---|---|---|---|---|---|
| [6] | 40, 77 | 4.9 | 4.9 | 0.01 - 1 k | 700 - 10 k | 139 | 7.84 |
| [7] | 80 | 0.291 | 2400 (5 V) | DC | 5 k | 82 | 3.57 |
| [8] | 40 | 2.2 | 12 (1 V) | 0.3 | 10 k | 80 | 2.9 |
| [9] | >100 | 1.9 (10 kHz) | 576 (1.8 V) | DC | 20 k | >99 | 12.9 |
| Prev. [3] | 41 - 45 | 0.8 - 2.7 | 3.3 - 3300 | 0.2 - 10 k | 38 - 11 k | 78 | 8.9 - 15 |
| This work | 40 - 60 ?? | XX - XX ? | XX - XX ? | 1 - 10 k ?? | 158 - 20 k?? | XX | XX ?? |

Fig. 16

DIGITAL BIOPOTENTIAL ACQUISITION SYSTEM HAVING 8 CHANNELS

RELATED APPLICATIONS

This application is the United States entry of International Application No. PCT/EP2017/054057, filed Feb. 22, 2017, which is related to and claims the benefit of priority of German Application No. 10 2016 103 073.2, filed Feb. 22, 2016. The contents of International Application No. PCT/EP2017/054057 and Gelman Application No. 10 2016 103 073.2 are incorporated by reference herein in their entireties.

FIELD

The invention relates to a biocompatible, neural implant for recording neural signals in a living being. In particular, the present invention discloses an acquisition system for neural signals within a chip for implantation in a living being.

BACKGROUND

A biopotential is an electrical potential that is measured between points in living cells, tissue and organisms and occurs in connection with all biochemical processes. It also describes the transfer of information between and within cells. It is an electrical quantity (voltage, current or field strength) that is caused by chemical reactions of charged ions. The term is further used in the description of the transfer of information between and within cells, for example in signal transmission.

Neural implants can electrically stimulate, capture and block (or even simultaneously capture and stimulate) signals from individual neurons or groups of neurons (biological neural networks) in a living being.

The present invention discloses the design and test of an integrated CMOS biopotential acquisition chip having 8 channels and consisting of a low-noise amplifier (LNA), a second stage, a multiplexer and two analogue-to-digital converters (ADC).

Due to its variable power consumption, the integrated noise of the first stage can be reduced from 1.94 to 0.693 $\mu V_{RMS}$ ($I_{SS}$=250 $\mu$A). The device has variable lower and upper corner frequencies and outputs two 16-bit digital data streams at 1 Mb/s.

The chip die is manufactured in X-Fab 0.35 $\mu$m CMOS technology and has an area of 10 mm².

Neural implants are devices that support the treatment of diseases such as Parkinson's disease, hearing impairments and heart defects.

Such devices connect the neural system by electrical stimulation to induce a reaction of the body. For example, cochlear implants stimulate the auditory nerve to create the sensory impression of hearing, pacemakers stimulate the inner wall of the heart to trigger heart muscle contractions, and deep brain stimulators generate signals that prevent unwanted muscle twitches caused by Parkinson's disease.

Medical research aims to understand how neural implants should affect the neural system. Normally, large recording systems are used in experiments on humans and animals that make it possible to visualize and process signals from the brain or nerves. Current experiments show a clear tendency towards the use of implantable acquisition systems, as they are one step closer to the reality of medical implants.

Depending on the type of application, bioelectric signals cover a wide range of amplitudes, noise levels and frequency bands. For this reason, a recording system that can adapt its properties to the respective applications is extremely desirable.

Ghovanloo shows a system with an extremely low power consumption that can detect brain signals and includes a variable bandwidth and radio transmission. M. Yin and M. Ghovanloo, "A low-noise clockless simultaneous 32-channel wireless neural recording system with adjustable resolution," *Analog Integrated Circuits and Signal Processing*, vol. 66, no. 3, S. 417-431, ISI:000287319400010, 2011. Harrison et al. shows a versatile acquisition amplifier which has proven itself in the case of brain action potentials, electroencephalography (EEG), electrocardiography (ECG) and electromyography (EMG).

A disadvantage of these acquisition systems is their noise level of 4 $\mu V_{RMs}$ and 2 $\mu V_{RMS}$ each, which is relatively high in applications with EEG and electroneurography (ENG).

Amplifiers also generate noise, which is divided into thermal noise and flicker noise.

The thermal noise density is constant with respect to the frequency and is proportional to the equivalent resistance of the transistor.

The flicker noise density, on the other hand, depends on the frequency with a factor of 1/f and is inversely proportional to the transistor surface.

Some effort has already been put into overcoming noise limitation. A notable work is represented by the BJT input transconductance operational amplifier (OTA) for ENG, proposed by R. Rieger and N. Donaldson.

Since BJT transistors do not generate flicker noise, the resulting input-related noise of 300 $nV_{RMS}$ is significantly lower than that of previous amplifiers. However, this architecture has two serious disadvantages:

1. It has a residual DC current of 20 nA from the electrode-tissue interface, which in the long term can lead to corrosion at the contacts, and
2. The technology is "open loop", which causes the gain to be a random variable, which may be a problem for the "True Tripole arrangement" used for a cuff electrode recording.

In addition, a chopper structure was proposed that shifts the signal to a frequency at which the flicker noise is negligible. The signal is then demodulated without flicker noise. Unfortunately, the chopper amplifier needs at least ten times more bandwidth to ensure that the signal is sufficiently far away. This requirement increases the power consumption of the amplifier.

SUMMARY

The present invention shows a versatile, low-noise amplifier to achieve an input noise level of sub-$\mu V_{RMS}$. The applied approach to noise reduction consists in an appropriate transistor size and power and in using PMOS input transistors with a lower flicker noise constant. The present system shown in FIG. 1 has 8 bipolar input channels and two independent serial digital outputs with two 10-bit ADCs.

BRIEF DESCRIPTION OF THE DRAWING FIGURES

FIG. 9 is a diagram of I/O pins of an LNA8 chip in accordance with the present disclosure;

FIG. 16 shows a comparison of a low-noise amplifier (LNA) according to the present disclosure with other systems;

DETAILED DESCRIPTION

LNA Preamplifier

It is known that the first stage (preamplifier) is the most important stage in an amplifier chain, as it is the component which is most susceptible to noise. For this reason, a fully-differential telescopic architecture has been used.

Figure 1:
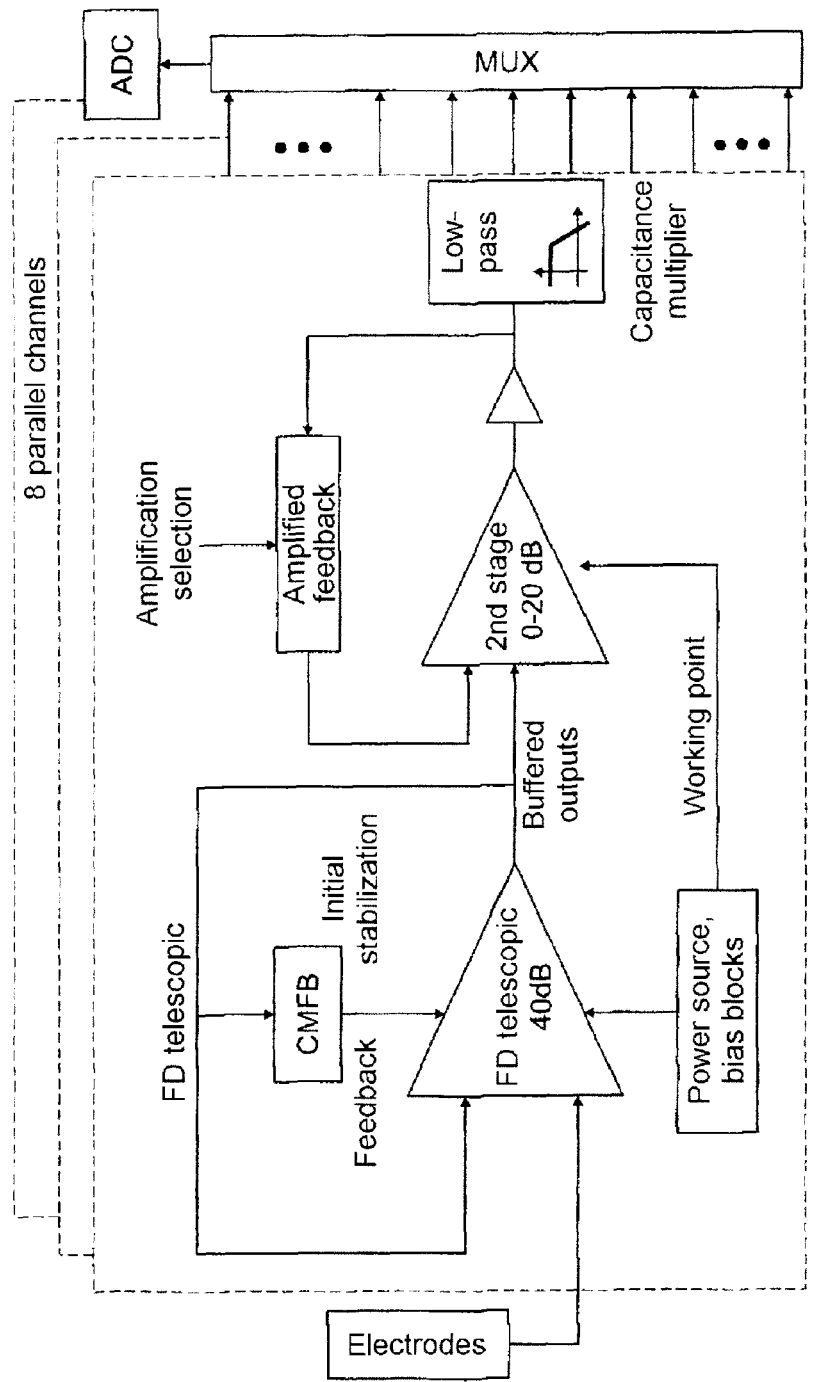
FIG. 1 is a block diagram of a recording system in accordance with the present disclosure.
Figure 2B:
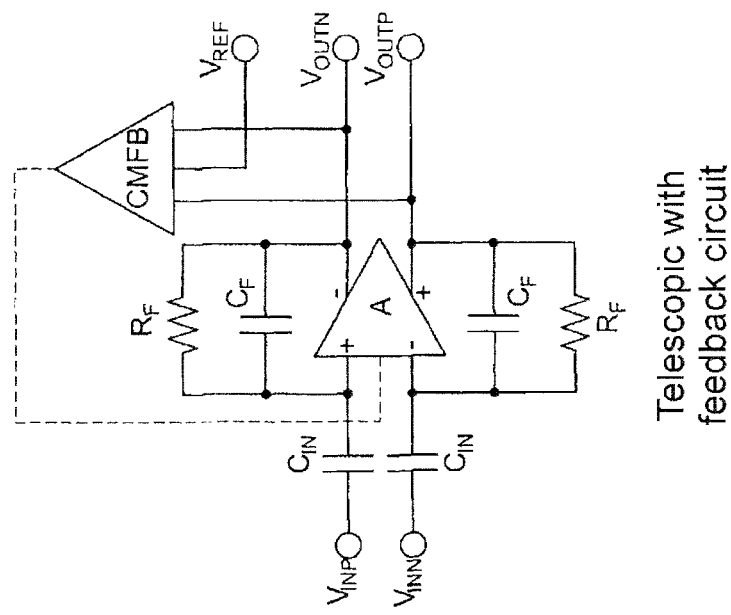
FIGS. 2A and 2B are diagrams of an architecture in accordance with the present disclosure.
Figure 2A:
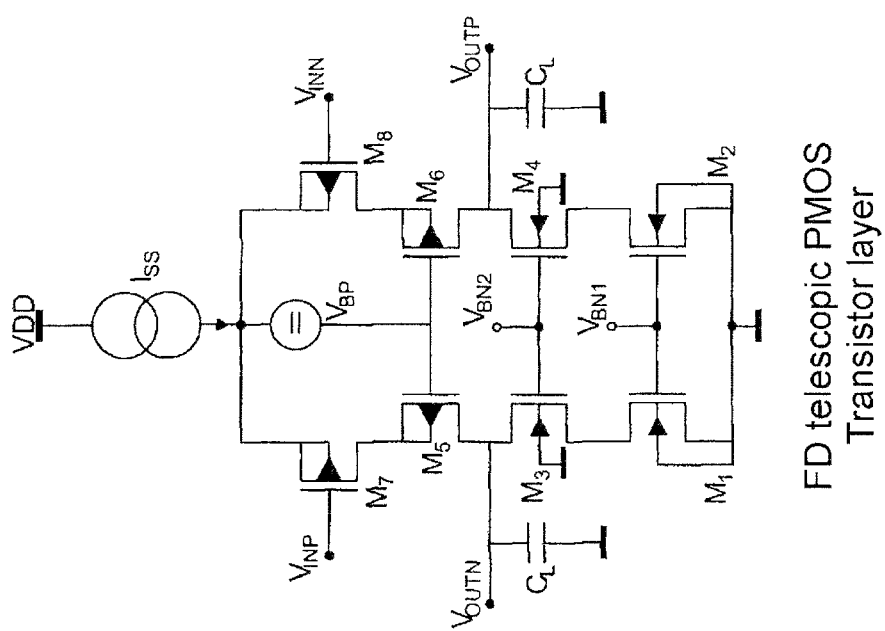

The architecture shown in FIGS. 2a and 2b provides high gain and bandwidth in a single stage and theoretically an infinite common mode rejection ratio (CMRR) and infinite noise suppression (PSRR).

The equations of the amplifier channels are known, and rephrased for the $g_m/I_D$ design methodology, the noise model is as follows:

$$\overline{V_{n,in}^2} = \frac{16kT(\Delta f - 1)}{3\left(\frac{g_m}{I_D}\right)_{1,2}} \left(1 + \frac{\left(\frac{g_m}{I_D}\right)_{7,0}}{\left(\frac{g_m}{I_D}\right)_{1,2}}\right) \frac{1}{I_D} + \frac{2\ln\Delta f}{C_{ox}} \left(\frac{K_n}{(WL)_{1,2}} + \frac{K_P}{(WL)_{7,8}} \left[\frac{\left(\frac{g_m}{I_D}\right)_{7,0}}{\left(\frac{g_m}{I_D}\right)_{1,2}}\right]^2\right) \quad (1)$$

And the transfer function:

$$H(s) = 2\frac{C_{IN}}{C_F} \frac{\frac{s}{2\pi f_{cL}}}{\left(1 \left|\frac{s}{2\pi f_{cL}}\right.\right)\left(1 \left|\frac{s}{2\pi f_{cL}}\right.\right)'} \quad (2)$$

with $$f_{cL} = \frac{1}{2\pi R_F C_F}; \quad f_{cU} = \frac{C_F}{C_{IN}} \frac{g_{m1,2}}{\pi C_l} = \frac{C_F}{C_{IN}} \frac{\sqrt{\beta_{1,2}}}{\pi C_L} \sqrt{I_{SS}} \quad (3)$$

Legend:

| | | | |
|---|---|---|---|
| Kn | Glitter noise constant | NMOS | $120 \times 10^{-24}$ V$^2$F |
| Kp | Glitter noise constant | PMOS | $20 \times 10^{-24}$ V$^2$F |
| k | Boltzmann's constant | | $1,3806 \times 10^{-23}$ m$^2$kg/s$^2$K |

(1)

| | | |
|---|---|---|
| $V^2_{n,in}$ | Total input noise | $V_{RMS}$ |
| k | Boltzmann's constant | 1 |
| T | Temperature | K |
| gm | Transconductance | A/V |
| ID | Current level at drain terminal | A |

(2)

| | | |
|---|---|---|
| $C_{IN}$ | Input capacity | F |
| $C_F$ | Feedback capacity | F |
| $f_{cL}$ | lower corner frequency | Hz |
| $f_{cU}$ | upper corner frequency | Hz |

-continued

| | (3) | |
|---|---|---|
| $R_F$ | Feedback resistance | Ω |
| β | MOSFET transistor current amplification | A/V² |
| $I_{SS}$ | Polarization current for FD telescope amplifier | A |

Figure 3:
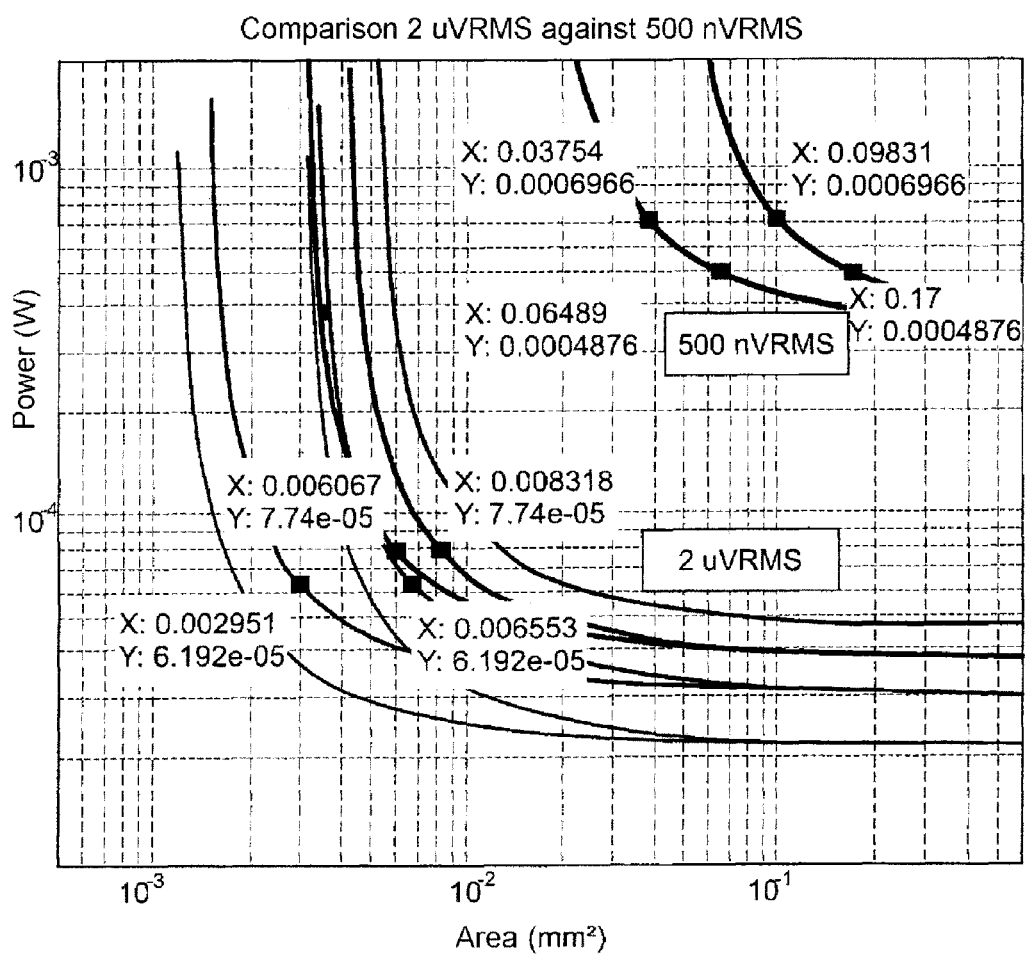
FIG. 3 is a graph of performance curves for predefined noise behavior.

Using the PMOS transistors and the optimal point marked in FIG. 3, the variables shown in Table 1 below were determined:

TABLE 1

Variables of the PMOS FD telescope amplifier

| | FD-telescopic Parameter | |
|---|---|---|
| Variables | W [μm] | L [μm] |
| $M_{1,2}$ | 8000 | 1.5 |
| $M_{3,4}$ | 1728 | 0.5 |
| $M_{5,6}$ | 168 | 1 |
| $M_{7,8}$ | 288 | 24 |
| Load capacity | 30.5 pF | |
| Bias current $I_{ss}$ | 205 μA | |
| Active surface | 0.04 mm² | |
| Layout surface | 0.15 mm² | |
| Channel surface | 2028 × 720 μm² | |

Second Stage

Figure 4:
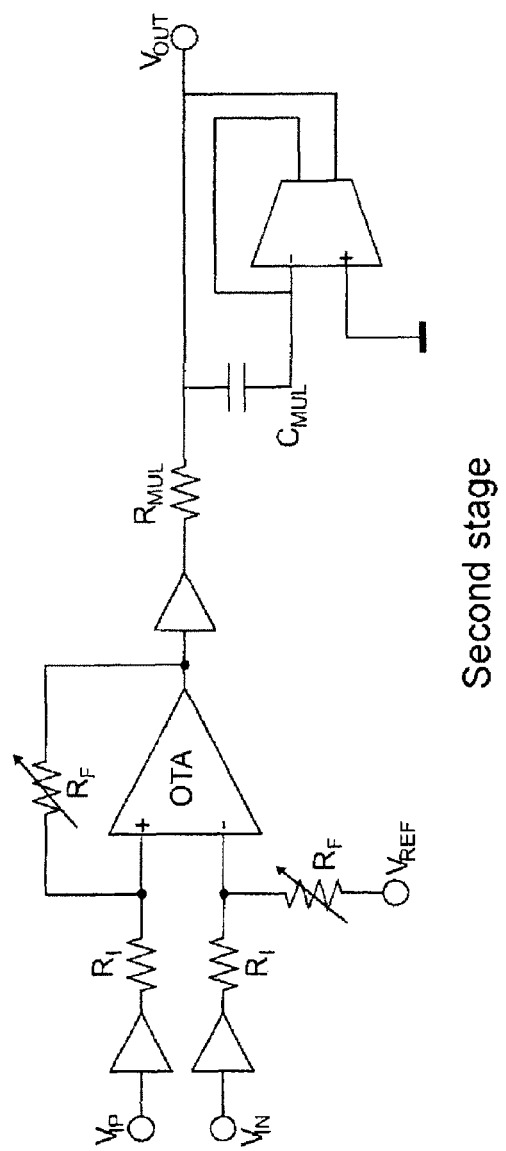
FIG. 4 is a block diagram of a second stage in accordance with the present invention.
Figure 5:
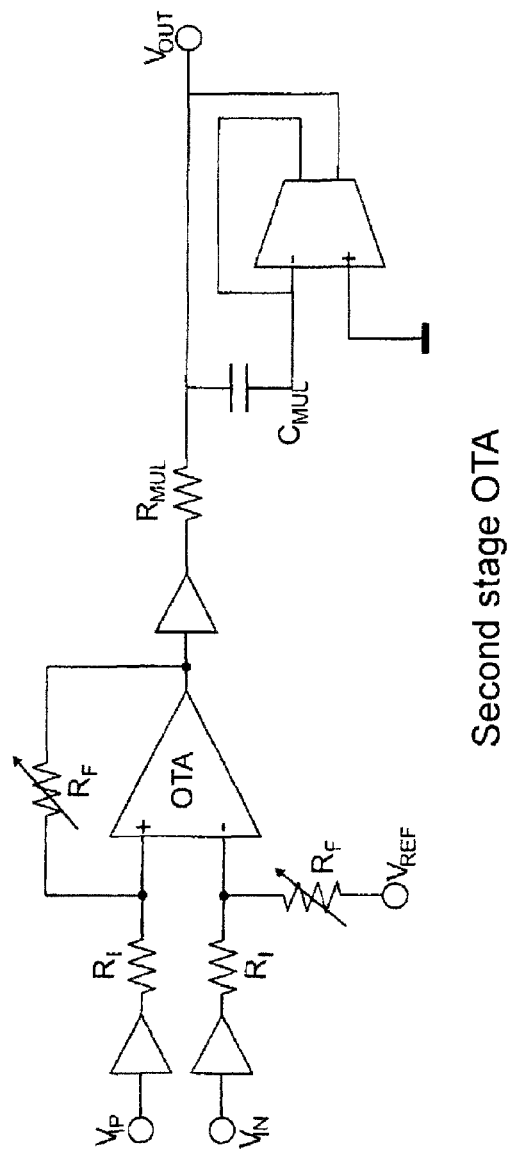
FIG. 5 is another block diagram of a second stage in accordance with the present invention.
Figure 6:
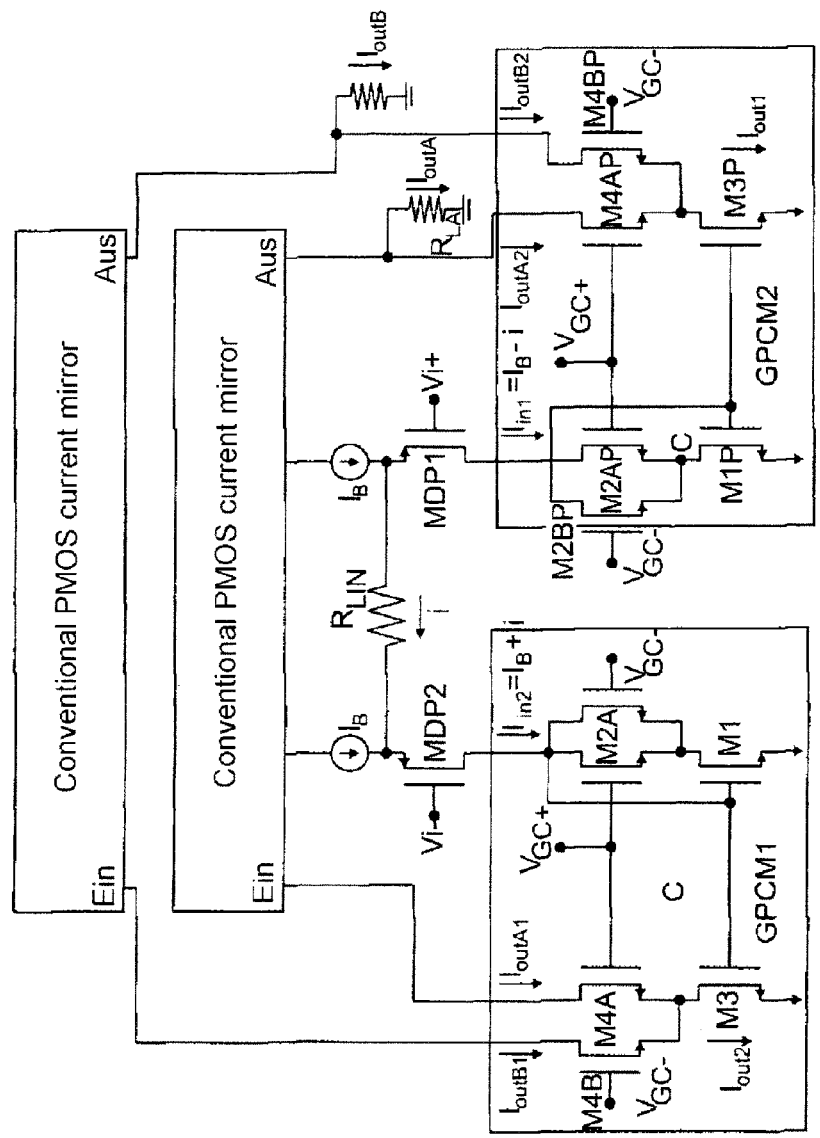
FIG. 6 is a block diagram of a control current capacitance multiplier.
Figure 7:
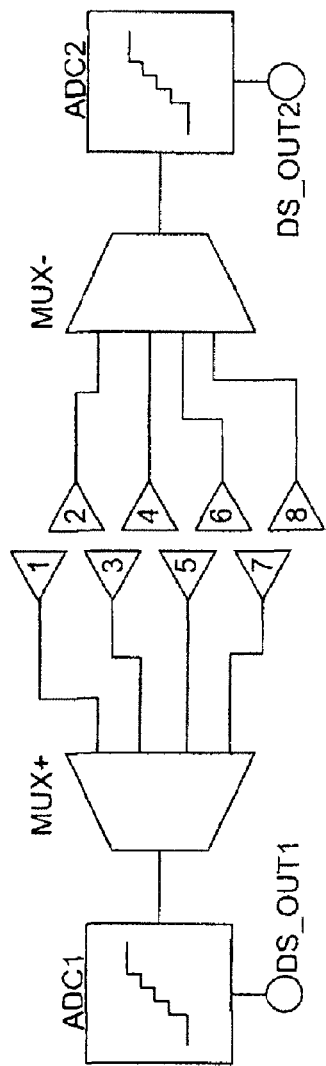
FIG. 7 is a block diagram of signal paths from amplifier outputs to serial digital outputs.

The second stage shown in FIG. 4 is responsible for the conversion from FD (fully differential) to single-ended, with an input noise in an amount of 6 $\mu V_{RMS}$ for a power consumption of 148 μW (11 $\mu V_{RMS}$ and 46 μW in LP mode). Due to feedback, it delivers a gain of either 0 dB or 20 dB. The OTA consists of a single-ended 2-stage Miller amplifier.

In the field of electronics, the Miller effect is the increase in the equivalent input capacitance of an inverting voltage amplifier due to the amplification of the effect of the capacitance between the input and output terminals. The apparently increased input capacity due to the Miller effect results as follows:

$$C_M = C(1+A_v)$$

where $-A_v$ is the gain and C is the feedback capacitance.

Although the term Miller effect usually refers to capacitances, any impedance connected between the input and another node showing gain can modify the amplifier input impedance with this effect.

Low-Pass Filter with Capacitance Multiplier

Since different applications require different upper corner frequencies fcu, a variable RC low-pass filter has been integrated.

In one reference, this variation was achieved by adjusting the LNA bias current Iss, creating a variation of the noise behavior. O. F. Cota, et al., "In-vivo characterization of a 0.8-3 \muV RMS input-noise versatile CMOS pre-amplifier," *Neural Engineering (NER)*, 2015 *7th International IEEE/EMBS Conference on,* 2015, S. 458-461. To avoid this unwanted coupling, a capacitance multiplier was proposed which uses the control current OTA from J. Ramirez-Angulo, et al., "Gain programmable current mirrors based on current steering," *Electronics Letters*, vol. 42, no. 10, S. 559-560, 2006 and which is connected to the second stage as is described in J. A. Ruiz, et al., "Three novel improved CMOS capacitance scaling schemes," in *Circuits and Systems (ISCAS), Proceedings of* 2010 *IEEE International Symposium on,* 2010, S. 1304-1307. The capacitance multiplication factor (from 50 pF to 5 nF) is set by the differential input $V_{GC\pm}$, the bias current of 56 μA and an area of 0.013 mm².

MUX, Analog-to-Digital Converter and Serial Output

The chip uses the X-Fab 0.35 μm library 10-bit SAR-ADC and integrates a user-defined flip-flop-based parallel-serial converter. The 16-bit little-endian output is combined as in J. Ramirez-Angulo, S. R. Garimella, A. J. López-Martin, and R. G. Carvajal, "Gain programmable current mirrors based on current steering," *Electronics Letters*, vol. 42, no. 10, S. 559-560, 2006, where S represents the start token bits (H L), bits C3-C0 represent the channel number and bits D9-D0 represent the ADC sample values.

Power Consumption

The power consumption of the chip is summarized in Table 2:

TABLE 2

| (*sim values) | 1 St [mW] | 2 St + Bias. | Cap. mult. (mW) | ADCs | Total (sim) mW |
|---|---|---|---|---|---|
| 29 μA | 0.765 | 2.03 | 1.19 | 0.495 | 4.49 |
| 29 μA LP | | 1.23 | (optional) | | 3.68 |
| 210 μA | 5.54 mW | 2.03 | 1.19 | | 9.26 |
| 210 μA | | 1.23 | (optional) | | 8.46 |
| 271 μA | 7.15 mW | 2.03 | 1.19 | | 10.87 |
| 271 μA | | 1.23 | (optional) | | 10.06 |

Result

Figure 8:
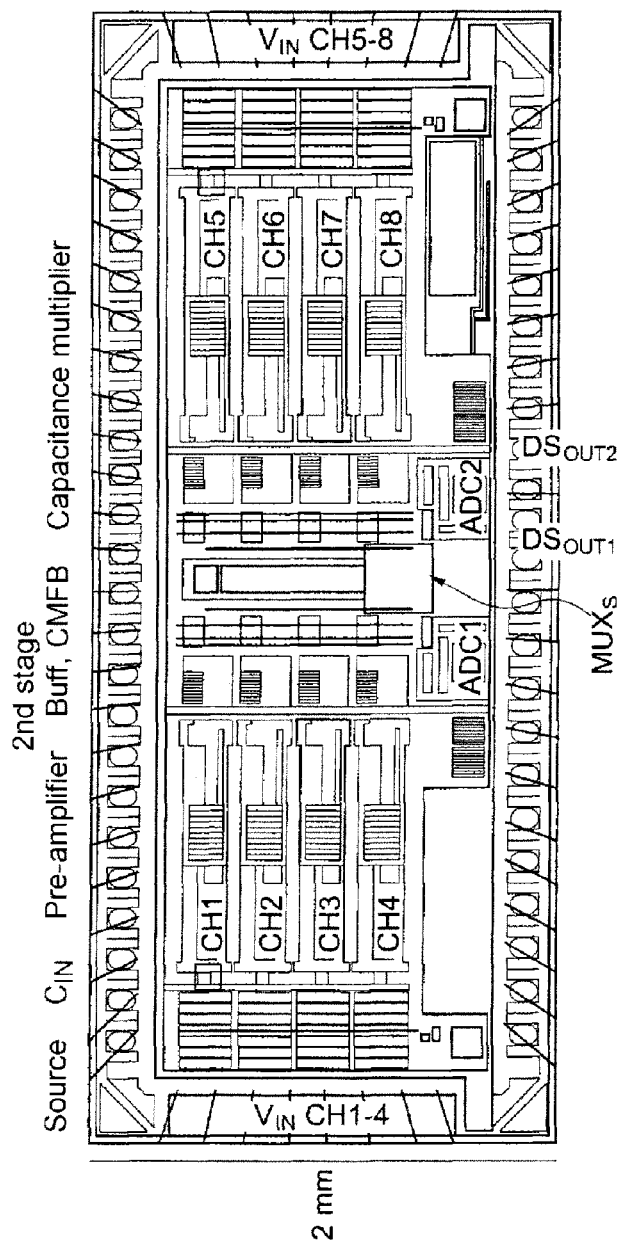
FIG. 8 is a schematic image of a chip with 8 bipolar input channels in accordance with the present disclosure.
Figure 10B:
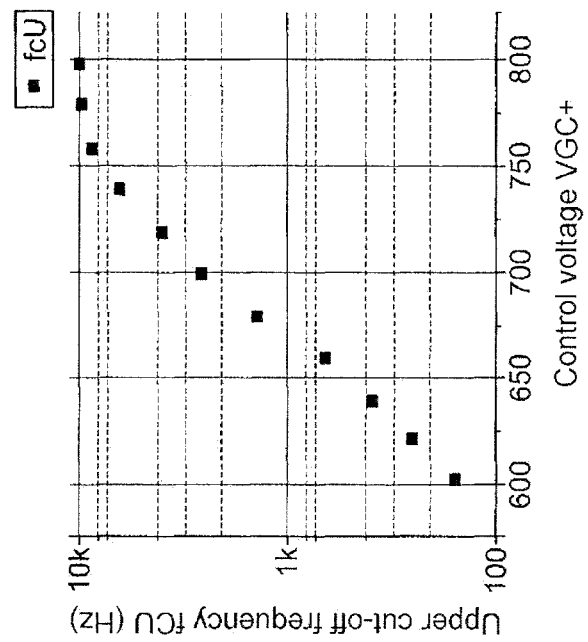
FIG. 10B is a graph showing variation of upper cut-off frequency via control of the bas VGC+ of the capacitance multiplier in accordance with the present disclosure.
Figure 10A:
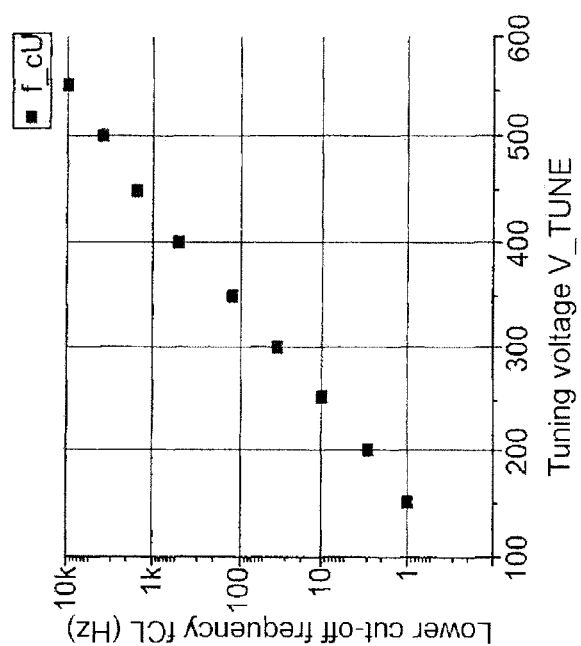
FIG. 10A is a graph showing variation of lower cut-off frequency via VTune in accordance with the present disclosure.
Figure 11:
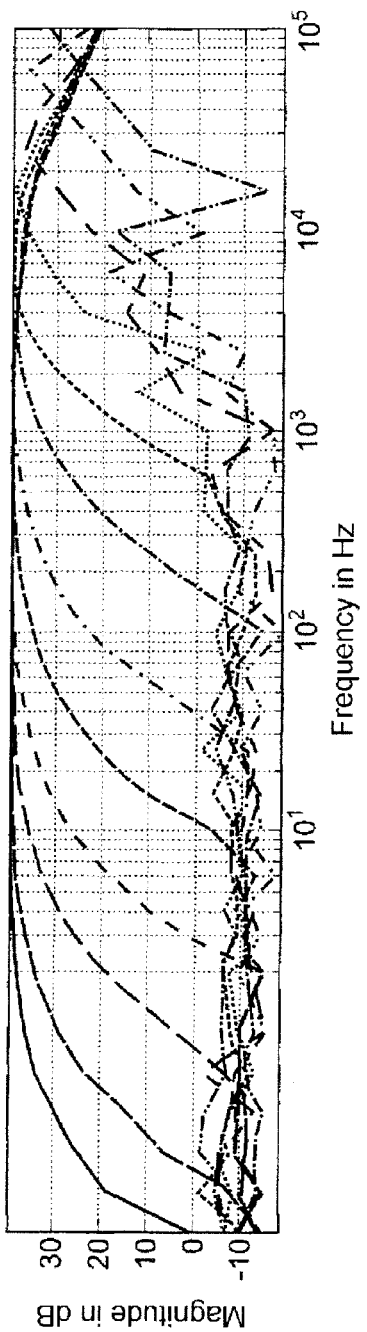
FIG. 11 is a first graph showing frequency versus magnitude in accordance with the present disclosure.
Figure 12A:
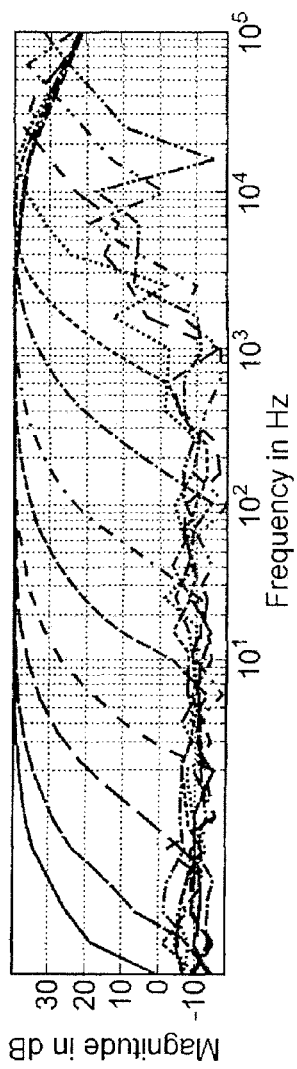
FIG. 12A is a second graph showing frequency versus magnitude in accordance with the present disclosure.
Figure 12B:
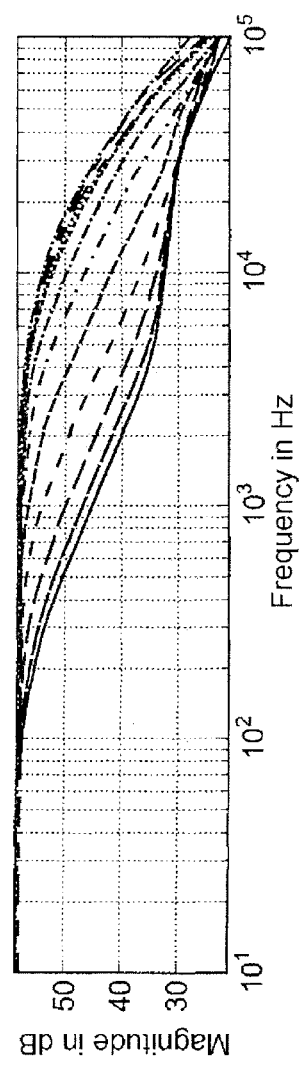
FIG. 12B is a third graph showing frequency versus magnitude in accordance with the present disclosure.
Figure 12C:
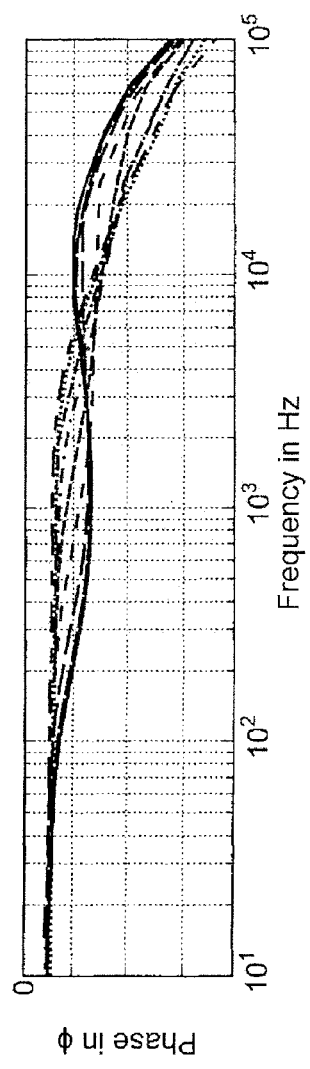
FIG. 12C is a graph showing frequency versus phase in accordance with the present disclosure.

The chip shown in FIG. 8 is manufactured using X-Fab 0.35 μm technology. The amplifier I/O pins are summarized in Table 2. The system pins offer flexibility for the parameters:

Enable function: continuous ISS variation, second stage low-power (LP) mode, capacitance multiplier, 20 dB gain Bias voltage: $V_{REF\_ISS}$, $V_{REF\_CMFB}$ Frequency range variation: $V_{GCP/N}$, $V_{TUNE}$ Although the chip is designed for digital output, it contains test pins to support its characterization, such as the analog outputs of the preamplifier and the low-pass filter of channels 1 and 5.

Table 3, below, shows I/O pins of the LNA8 chip. Underlined pins represent outputs.

TABLE 3

| Analog | | Digital | |
|---|---|---|---|
| (D, A)$V_{DD}$ | 3 | $I_{SS}$(T1-T4) | 4 |
| (D, A)$V_{SS}$ | 3 | V_REF_ISS_EN | |
| $V_{REF\ ISS}$ | | LP EN | |
| VIN(N/P)(1-8) | 16 | RESET EN | |
| $V_{REF\ CMFB}$ | | GAIN_0dB_EN | |
| $V_{GCP/N}$ | 2 | CAP MULT EN | |
| $V_{TUNE}$ | | CLK | |
| $V_{REFH}$ | | CHSEL$_{0-3}$ | 4 |
| $V_{REFL}$ | | DSOUT(½) | 2 |
| Test (analog) | | | |
| $V_{EXTCMFB}$ | | | |
| $V_{DDISS(1,\ 5)}$ | | 2 | |
| $V_{OUTN/P(1,\ 5)}$ | | 2 | |
| $V_{OUT1/5}$ | | 2 | |
| Test (digital) | | | |
| RESET ADC | | | |
| Q1$_{0-3}$ | | 4 | |
| EOC1 | | | |
| SW1 | | | |

The ADCs can be clocked with two serial digital outputs up to 1 MHz.

Frequency Response

The LNA8 recording system has variable corner frequencies fcU, fcL in each case by varying the potentials $V_{TUNE}$ and $V_{GC\pm}$.

Noise Behavior

The spectral noise density of the amplifier was measured for different bias currents and bandwidth setting voltages.

Figure 13:
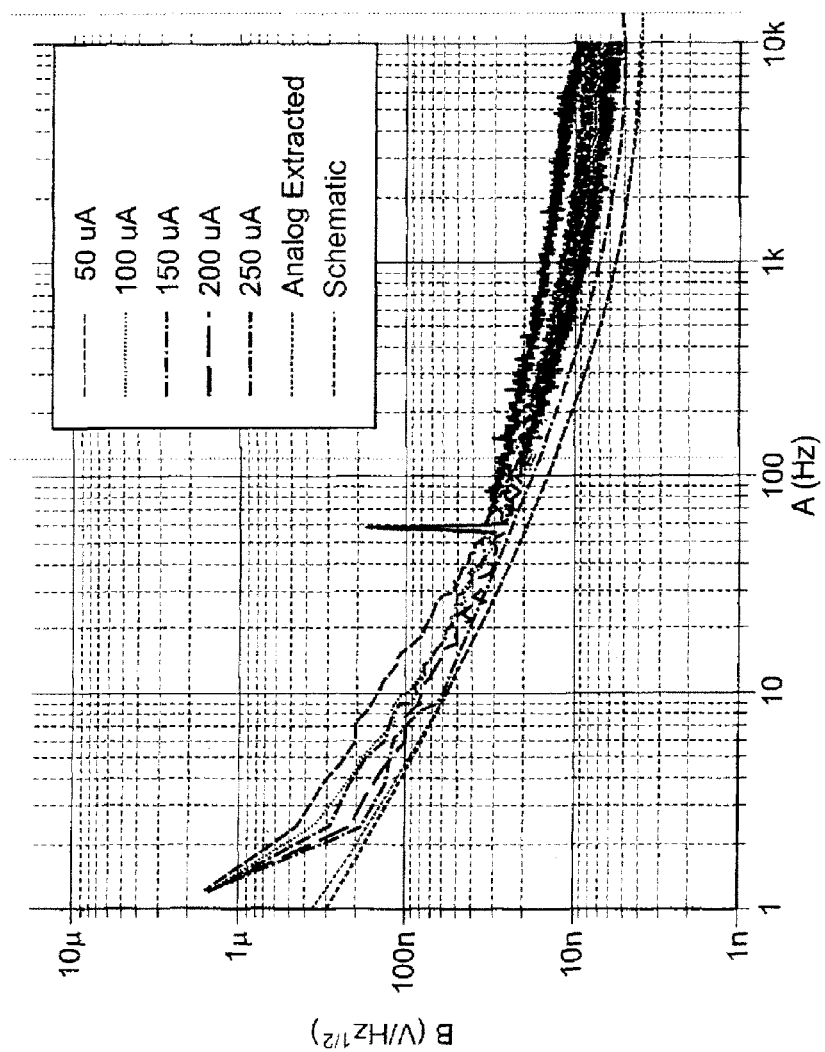
FIG. 13 is a graph showing measured curves in comparison to schematic and analog extracted simulations.
Figure 14:
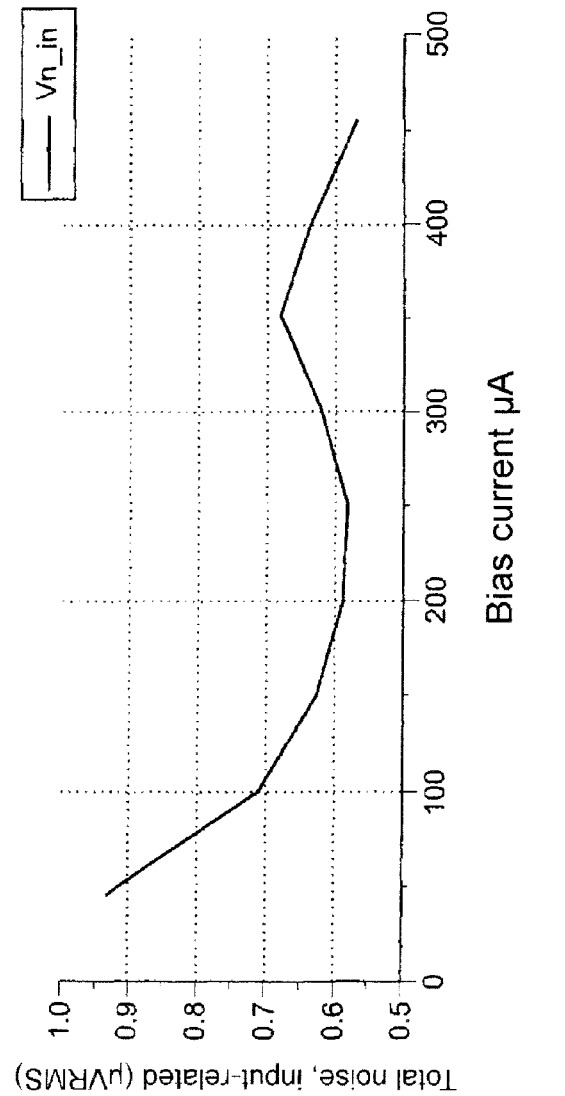
FIG. 14 is a graph showing total integrated input noise for different amplifier configurations.

The graphical representation in FIG. 13 shows the measured curves in comparison to the schematic and analog extracted simulations. FIG. 14 shows the total integrated input noise for different amplifier configurations. The curve shows a minimum noise of *(sim. value) 0.6 $V_{RMS}$ for $I_{SS}$=250 μA.

In Vivo Recording

The acquisition system has been tested with bioelectric in-vivo signals as shown in FIG. 15. The bioelectric signals were extracted directly from the serial digital outputs using SPI decoding. The SPI bus (Serial Peripheral Interface) is a synchronous, serial communication interface specification used for short-range communication. SPI devices can communicate with a single master in full duplex operation using a master-slave architecture. The master device generates the frame for reading and writing. A multitude of slave devices are supported by selection with individual slave select lines (SS).

Figure 15A:
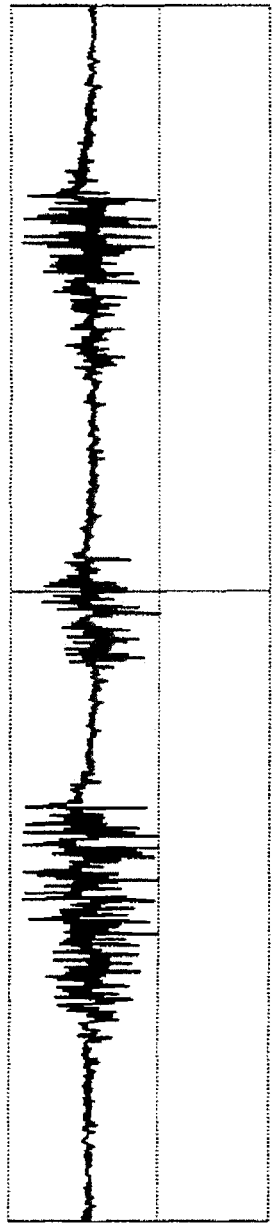
FIG. 15A is an image of three successive contractions of an exemplary biceps by EMG detection.
Figure 15B:
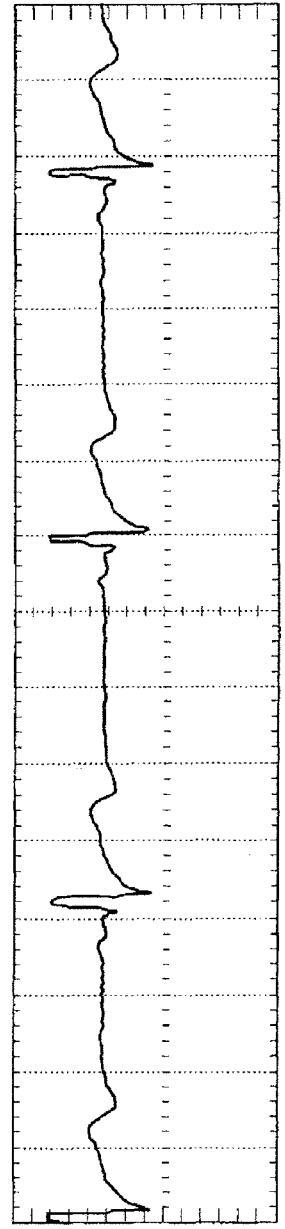
FIG. 15B is an image of three successive contractions of an exemplary biceps by ECG detection.
Figures 17A, 17B:
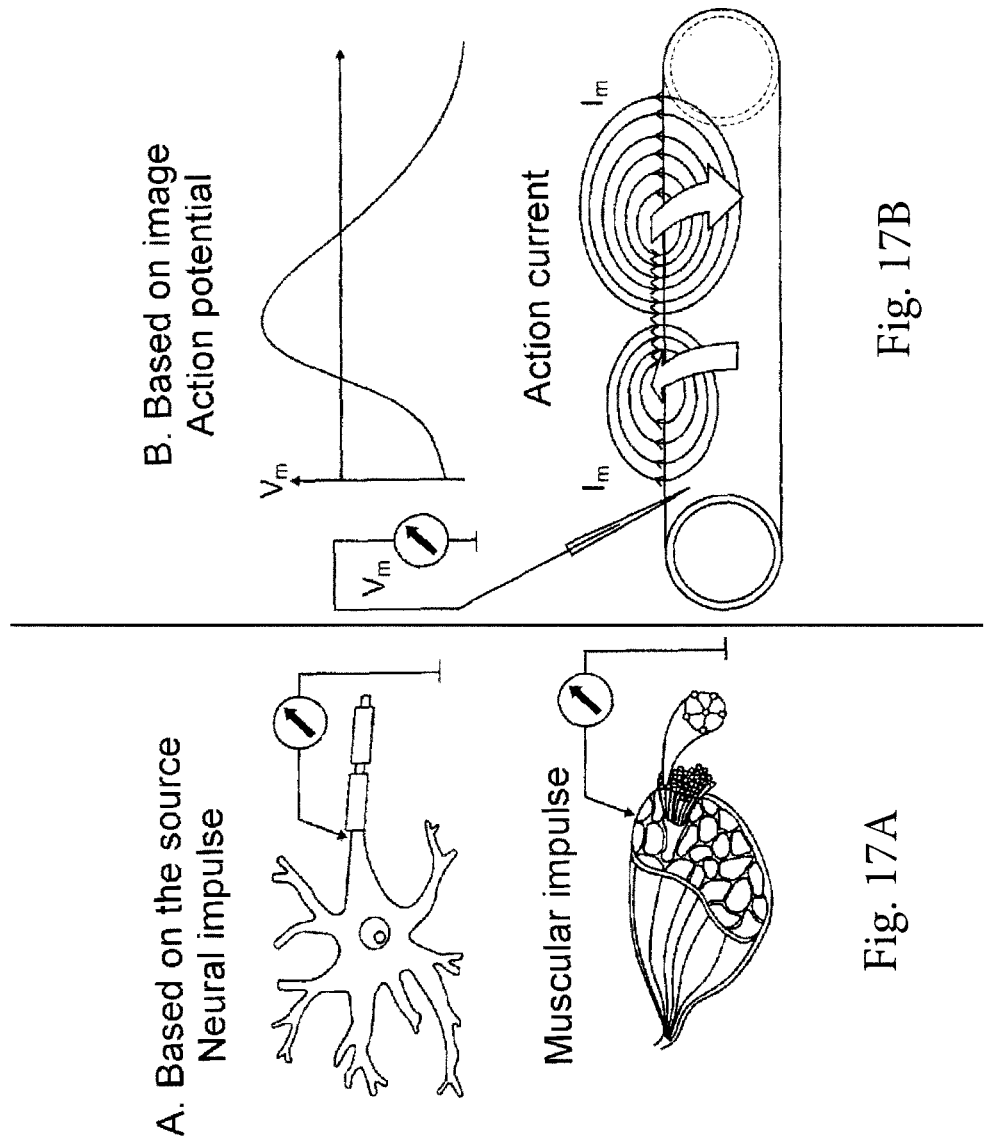
FIG. 17A are diagrams based on the source neural impulse and muscular impulse.
FIG. 17B are diagrams based on image action potential and action current.

FIG. 15A shows three successive contractions of an exemplary biceps EMG detection. FIG. 15B shows an ECG detection.

The foregoing description shows the implementation of a biopotential acquisition system with 8 channels.

Although the best noise efficiency factor is achieved by the design that uses BJT transistors, this has the disadvantage that a residual DC current of 20 nA remains, which can lead to electrode corrosion in the long run.

The capacitance multiplier fulfilled its function of providing a wide range for the upper cut-off frequency.

However, since it was dimensioned for minimum area and power consumption, the noise behavior could not be kept below 1 $\mu V_{RMS}$ without a capacitance multiplier; the noise behavior can be maintained by software filtering.

Table 4 shows a comparison of the shown low-noise amplifier (LNA) with other systems.

TABLE 4

| System | Amplification/db | Noise/$\mu V_{RMS}$ | Power/Channel/μW | fcL/Hz | fcU/Hz | CMRR/db | NRF |
|---|---|---|---|---|---|---|---|
| M. Yin and M. Ghovanloo | 40; 77 | 4.9 | 49 | 0.01-1k | 700-10k | 139 | 7.84 |
| J. Taylor and R. Rieger | 80 | 0.291 | 2400 (5 V) | DC | 5k | 82 | 3.57 |
| F. Zhang, et al. | 40 | 2.2 | 12 (IV) | 0.3 | 10k | 80 | 2.9 |
| [9] | >100 | 1.9(10 kHz) | 576 (1.8 V) | DC | 20k | >99 | 12.9 |
| Before O. F. Cota, et al. | 41-45 | 0.8-2.7 | 3.3-3300 | 0.2-10k | 38-11k | 78 | 8.9-15 |
| Present Design | 39.3 or 58.4 | 1.94-0.69* (sim val) | 303-1200* (sim) | 0.1-10k | 200-20k | 60.3; 74 | 3.52 (1. stage) 6.57 (2. stage) |

Compared to the previous work in O. F. Cota, et al., the present design integrated the other blocks of the desired system.

The amplifier area has been reduced by a factor of four and an analog output.

Result

The invention shows the successful implementation and the testing of a versatile bioelectric signal acquisition chip with 8 channels. The amplified channels are selected from two analog multiplexers and are output by two SPI-compatible 16-bit data streams. The total integrated input noise can be reduced to *(sim. value) 0.6 $\mu V_{RMS}$ for bandwidths between 1 Hz and 10 kHz. The acquisition system has been tested for ECG and EMG applications.

The invention claimed is:
1. A biocompatible recording system for acquiring electronic information from a neural system of a living being, the recording system comprising:
   a first amplifier stage consisting of a pre-amplifier;
   a second amplifier stage, wherein an input of the second amplifier stage is coupled to an output of the preamplifier; and a low pass filter having a capacitance multiplier connected to the second amplifier stage, wherein the recording system has variable lower (fcL) and upper (fcU) corner frequencies by variation of predetermined signals, the lower (fcL) corner frequencies being based on variation by a tuning voltage (VTUNE) and the upper (fcU) corner frequencies being based on variation by a control voltage (VGC±).

2. The recording system according to claim 1, wherein the preamplifier uses P-MOS input transistors in the first amplifier stage.

3. The recording system according to claim 1, wherein the recording system is configured to acquire at least two signals independently of one another with at least two recording channels.

4. The recording system according to claim 1, wherein the capacitance multiplier is configured to provide a range for the upper (fcU) corner frequencies between 1 Hz and 10 kHz and a noise reduction below 1 $\mu V_{RMS}$.

5. The recording system according to claim 1 comprising a flip-flop-based parallel-serial converter that is integrated into the recording system.

6. The recording system according to claim 1, wherein the second amplifier stage delivers a gain of either 0 dB or 20 dB due to feedback.

7. A biocompatible recording system for acquiring electronic information from a neural system of a living being, the recording system comprising:

a first amplifier stage consisting of a preamplifier with a fully-differential telescopic architecture;

a second amplifier stage, wherein an input of the second amplifier stage is coupled to an output of the preamplifier; and a low pass filter having a capacitance multiplier connected to the second amplifier stage, wherein the recording system has variable lower (fcL) and upper (fcU) corner frequencies by variation of predetermined signals, the lower (fcL) corner frequencies being based on variation by a tuning voltage (VTUNE) and the upper (fcU) corner frequencies being based on variation by a control voltage (VGC±).

* * * * *